(12) United States Patent
Brighton et al.

(10) Patent No.: US 7,167,753 B2
(45) Date of Patent: Jan. 23, 2007

(54) DEVICE AND METHOD FOR ELECTRICALLY INDUCING OSTEOGENESIS IN THE SPINE

(75) Inventors: Carl T Brighton, Malvern, PA (US); Solomon R Pollack, North Wales, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/482,313

(22) PCT Filed: Jul. 2, 2002

(86) PCT No.: PCT/US02/20927

§ 371 (c)(1),
(2), (4) Date: Dec. 16, 2004

(87) PCT Pub. No.: WO03/004092

PCT Pub. Date: Jan. 16, 2003

(65) Prior Publication Data

US 2005/0125045 A1    Jun. 9, 2005

Related U.S. Application Data

(60) Provisional application No. 60/302,846, filed on Jul. 3, 2001.

(51) Int. Cl.
*A61N 1/40* (2006.01)
(52) U.S. Cl. .......................... 607/51; 607/43
(58) Field of Classification Search ................ 607/43, 607/51, 117, 118
See application file for complete search history.

(56) References Cited

U.S. PATENT DOCUMENTS 4,430,999 A    2/1984   Brighton et al. ............ 128/419

(Continued)

FOREIGN PATENT DOCUMENTS

WO    WO 01/62336 A1    8/2001

(Continued)

OTHER PUBLICATIONS

Brighton, C.T., et al., "Signal transduction in electrically stimulated bone cells," *J. Bone Joint Surg. Am.*, 2001, 83-A(10), 1514-1523.

(Continued)

*Primary Examiner*—Jeffrey R Jastrzab
(74) *Attorney, Agent, or Firm*—Woodcock Washburn LLP

(57) ABSTRACT

A technique and associated device for stimulating multiple electrodes with multiple electrical signals in multiple regions of the spine without injury to the patient. The electrodes are applied to respective sides of the patient's spine, and a first electrical signal is applied to any electrodes in a treatment area of the lumbar region of the patient's spine, a second electrical signal is applied to any electrodes in a treatment area of the thoracic region of the patient's spine, and a third electrical signal is applied to any electrodes in a treatment area of the cervical region of the patient's spine to induce osteogenesis in at least one of the respective treated area's of the patient's spine. The first, second, and third electrical signals respectively generate different electrode currents in the respective treated areas and are ideally selected to create current densities that are approximately equal in respective treatment areas. The electrodes may include electrode pairs or strip electrodes placed either side of the patient's spine in the respective treatment areas.

25 Claims, 4 Drawing Sheets

U.S. PATENT DOCUMENTS

| | | | |
|---|---|---|---|
| 4,442,846 A | 4/1984 | Brighton et al. | 128/784 |
| 4,467,808 A | 8/1984 | Brighton et al. | 128/419 F |
| 4,467,809 A | 8/1984 | Brighton | 607/51 |
| 4,487,834 A | 12/1984 | Brighton | 435/173 |
| 4,506,674 A | 3/1985 | Brighton et al. | 128/419 |
| 4,509,520 A | 4/1985 | Dugot | 128/419 |
| 4,535,775 A | 8/1985 | Brighton et al. | 128/419 |
| 4,549,547 A | 10/1985 | Brighton et al. | 128/419 F |
| 4,600,010 A | 7/1986 | Dugot | 128/419 |
| 5,014,699 A | 5/1991 | Pollack et al. | 128/419 |
| 5,038,797 A | 8/1991 | Batters | 128/798 |
| 5,269,746 A | 12/1993 | Jacobson | 600/13 |
| 5,273,033 A | 12/1993 | Hoffman | 607/46 |
| 5,338,286 A | 8/1994 | Abbott et al. | 600/14 |
| 5,374,283 A | 12/1994 | Flick | 607/46 |
| 5,743,844 A | 4/1998 | Tepper et al. | 600/14 |
| 5,792,209 A * | 8/1998 | Varner | 607/51 |
| 6,083,149 A | 7/2000 | Wascher et al. | 600/9 |
| 6,132,362 A | 10/2000 | Tepper et al. | 600/14 |
| 6,186,940 B1 | 2/2001 | Kirschbaum | 600/12 |
| 6,261,221 B1 | 7/2001 | Tepper et al. | 600/14 |
| 6,292,699 B1 | 9/2001 | Simon et al. | 607/51 |
| 6,485,963 B1 | 11/2002 | Wolf et al. | 435/298.2 |
| 6,560,487 B1 * | 5/2003 | McGraw et al. | 607/51 |
| 2002/0052634 A1 | 5/2002 | March | 607/50 |
| 2003/0211084 A1 | 11/2003 | Brighton et al. | 424/93.7 |

FOREIGN PATENT DOCUMENTS

WO    WO 2005/070136 A2    8/2005

OTHER PUBLICATIONS

Pienkowski, D., et al., "Low-power electromagnetic stimulation of osteotomized rabbit fibuiae," *J. of Bone & Joint Surgery*, 1994, 76-A(4), 489-501.

Wang, W., et al., "Up-regulation of chondrocyte matrix genes and products by electric fields," *Clin. Orthopaedics & Related Res.*, 2004, 427S, S163-S173.

Chang, W.H., et al., "Enhancement of fracture healing by specific pulsed capacitively-coupled electric field stimulation," *Frontiers Med. Biol. Engng.*, 1991, 3(1), 57-64.

Aaron, R.K., et al., "The conservative treatment of osteonecrosis of the femoral head," *Clin. Orthop.*, 1989, 249, 209-218.

Aaron, R.K., et al., "Stimulation of experimental endochondral ossification by low-energy pulsing electromagnetic fields," *J. Bone Miner. Res.*, Nov. 2, 1989, 4, 227-233.

Bassett,C.A.L., "Low energy pulsing electromagnetic fields modify biomedical processes," *BioEssays*, 1987, 6(1), 36-42.

Bassett, C.A.L., et al., "Effects of pulsed electromagnetic fields on Steinberg ratings of femoral head osteonecrosis," *Clin. Orthop.*, Sep. 1989, 246, 172-185.

Bassett, C.A.L., et al., "Fundamental and practical aspects of therapeutic uses of pulsed electromagnetic fields (PEMSs)," *Crit. Rev. Biomed. Eng.*, 1989, 17(5), 451-529.

Bassett, C.A.L., et al., "Pulsing electromagnetic field treatment in ununited fractures and failed arthrodeses," *JAMA*, Feb. 5, 1982, 247(5), 623-628.

Binder, A., et al., "Pulsed electromagnetic field therapy of persistent rotator cuff tendonitis," *Lancet*, Mar. 31, 1984, 695-698.

Brighton, C.T., et al., "A multicenter study of the treatment of non-union with constant direct current," *J. Bone and Joint Surgery*, Jan. 1981, 62-A(1), 2-13.

Brighton, C.T., et al., "Treatment of recalcitrant non-union with a capacitively coupled electrical field," *J. Bone and Joint Surgery*, Apr. 1985, 67-A(4), 577-585.

Brighton, C.T., et al., "Treatment of castration-induced osteoporosis by a capacitively coupled electrical signal in rat vertebrae," *J. Bone and Joint Surgery*, Feb. 1989, 71-A(2), 228-236.

Brighton, C.T., et al., "Increased cAMP production after short-term capacitively coupled stimulation in bovine growth plate chondrocytes," *J. Orthop. Res.*, 1988, 6, 552-558.

Brighton, C.T., et al., "Treatment of denervation/disuse osteoporosis in the rat with a capacitively coupled electrical signal: effects on bone formation and bone resorption," *J. Orthop. Res.*, 1988, 6, 676-684.

Goodman, R., et al., "Exposure of salivary gland cells to low-frequency electromagnetic field alters polypeptide synthesis," *Proc. Natl. Acad. Sci. USA*, Jun. 1988, 85, 3928-3932.

Goodwin, C.B., et al., "A double-blind study of capacitively coupled electrical stimulation as an adjunct to lumbar spinal fusions," *Spine*, 1999, 24(13), 1349-1356.

Grodzinsky, A.J., "Electromechanical and physicochemical properties of connective tissue," *Crit. Rev. Biomed. Engng.*, 1983, 9(2), 133-198.

Harrison, M.H.M., et al., "Use of pulsed electromagnetic fields in perthes disease: report of a pilot study," *J. Pediatr. Orthop.*, 1984, 4, 579-584.

Jones, D.B., et al., "PEMF effects on differentiation and division in mirine melanoma cells are mediated indirectly through cAMP," *Trans. BRAGS 6*, 1986, 51.

Lorich, D.G., et al., "Biochemical pathway mediating the response of bone cells to capacitive coupling," *Clin. Orthop. and Related Res.*, 1998, 350, 246-256.

Massardo, L., et al., "Osteoarthritis of the knee joint: an eight year prospective study," *Ann Rheum Dis.*, 1989, 48, 893-897.

Mooney, V., "A randomized double-blind prospective study of the efficacy of pulsed electromagnetic fields for inter body lumbar fusions," *Spine*, 1990, 15(7), 708-712.

Norton, L.A., et al., "Pulsed electromagnetic fields alter phenotypic expression in chondroblasts in tissue culture," *J. Orthop. Res.*, 1988, 6, 685-689.

Rodan, G.A., et al., "DNA synthesis in cartilage cells is stimulated by oscillating electric fields," *Science*, Feb. 10, 1978, 199, 690-692.

Ryaby, J.T., et al., "Pulsing electromagnetic fields affect the phosphorylation and expression of oncogene proteins," *Trans. BRAGS 6*, 1986, p. 78.

Ryaby, J.T., et al., "The effect of electromagnetic fields on protein phosphorylation and synthesis in murine melanoma cells," *BRAGS*, p. 32.

Wang, W., et al., "The increased level of PDGF-A constributes to the increased proliferation induced by mechanical stimulation in osteoblastic cells," *Biochem. And Molecular Biol. International*, Oct. 1997, 43(2), 339-346.

Zhuang, H., et al., "Mechanical strain-induced proliferation of osteoblastic cells parallels increased TGF-β1 mRNA,"*Biochem. Biophys. Res. Commun.*, 1996, 229, 449-453.

Zhuang, H., et al., "Electrical stimulation induces the level of TGF-β1 mRNA in osteoblastic cells by a mechanism involving calcium/calmodulin pathway," *Biochem. Biophys. Res. Commun.*, 1997, 237, 225-229.

Brighton, C.T., et al., "Fracture healing in the rabbit fibula when subjected to various capacitively coupled electrical fields," *J. Orthop. Res.*, 1985, 3, 331-340.

Brighton, C.T., et al., "*In vitro* bone-cell response to a capacitively coupled electrical field," *Clin. Orthop. Related Res.*, Dec. 1992, 285, 255-262.

Carter, E.L., et al., "Field distributions in vertebral bodies of the rat during electrical stimulation: a parametric study," *IEEE Trans. on Biomed. Eng.*, Mar. 1989, 36(3), 333-345.

Brighton, C.T., et al., "Prevention and treatment of sciatic denervation disuse osteoporosis in rat tibia with capacitively coupled electrical stimulation," *Bone*, 1985, 6, 87-97.

Brighton, C.T., et al., "Treatment of nonunion of the tibia with a capacitively coupled electrical field," *J. of Trauma*, 1984, 24(2), 153-155.

Brighton, C.T., et al., "Tibial nonunion treated with direct current, capacitive coupling, or bone graft," *Clin. of Orthop. and Related Res.*, 1995, 321, 223-234.

\* cited by examiner

DEVICE AND METHOD FOR ELECTRICALLY INDUCING OSTEOGENESIS IN THE SPINE

CROSS-REFERENCE TO RELATED APPLICATIONS

This application is the National Stage of International application Ser. No. PCT/US02/20927, filed Jul. 2, 2002, which claims the benefit of U.S. Provisional application Ser. No. 60/302,846, filed Jul. 3, 2001.

BACKGROUND OF THE INVENTION

1. Field of the Invention

The present invention relates to a device and method for fusing multiple spine levels and otherwise increasing the stability of the spine through selective application of electrical signals.

2. Description of the Prior Art

U.S. Pat. No. 4,535,775 demonstrated that an appropriate capacitively coupled electric signal applied to a single pair of surface electrodes placed on the skin on each side overlying a bone defect, nonunion fracture, delayed union, fresh fracture, or fracture at risk produced an internal electric field in the bone that resulted in healing of the bone. This technology has also been successfully applied to the treatment of fracture nonunions and delayed unions and as an adjunct to the treatment of localized spine fusion (Fusion of 1–2 vertebral levels; for example $L_1$–$L_2$ and $L_2$–$L_3$). There continues to be a great need to be able to use electricity in its various forms to fuse multiple spinal levels as in spinal scoliosis, degenerative disk disease at multiple levels, spine instability secondary to trauma of any cause, spinal stenosis, osteoporosis and tumor, including pain symptoms associated with the above. The present invention addresses these needs.

SUMMARY OF THE INVENTION

The present invention addresses the above-mentioned needs in the art by determining the proper electric field amplitude and electrode placement for application of electric signals in the human spine to aid in spine fusion at multiple levels. To date, no animal or human data exists for such applications, and in order to obtain such data, a model was developed in the rat and then reconfigured for use in humans. The present invention relates to this model and its application to a human spine for electrically induced osteogenesis.

In particular, the present invention relates to a device and method of electrically inducing osteogenesis in the spine by placing electrodes on either side of the patient's spine and applying at least one of a first electrical signal to any electrodes in a treatment area of the lumbar region of the patient's spine, a second electrical signal to any electrodes in a treatment area of the thoracic region of the patient's spine, and a third electrical signal to any electrodes in a treatment area of the cervical region of the patient's spine effective to induce osteogenesis in at least one of the respective treatment areas of the patient's spine. In accordance with the invention, the first, second, and third electrical signals respectively generate different electrode currents in the respective treatment areas and create current densities that are approximately equal in the respective treatment areas when applied simultaneously. The electrodes may comprise respective pairs of electrodes placed in each of the treatment areas or strip electrodes that are applied to a single treatment area or across two or more treatment areas that run vertically along the patient's spine.

In a preferred embodiment, the current stimulated by the first electrical signal in the lumbar region is greater than the current stimulated by the second electrical signal in the thoracic region, and the current stimulated by the second electrical signal in the thoracic region is greater than the current stimulated by the third electrical signal in the cervical region. Preferably, the current stimulated by the second electrical signal is approximately ⅔ the current stimulated by the first electrical signal, and the current stimulated by the third electrical signal is approximately ⅔ the current stimulated by the second electrical signal. For example, the electrode current stimulated by the first electrical signal may be in the current range of 7–10 mA, the electrode current stimulated by the second electrical signal may be in the current range of 4.7–6.7 mA, and the electrode current stimulated by the third electrical signal may be in the current range of 3.1–4.5 mA.

The power source of the invention generates the first, second and third electrical signals and further comprises at least one switch that selectively applies the first, second or third electrical signals to respective electrode pairs in accordance with the treatment area of the spine in which the respective electrode pairs are placed. In the case of strip electrodes, the strip electrodes may be discontinuous whereby each two vertebra length of strip electrode receives one of the first, second and third electrical signals from the power source based on whether the two vertebra length is placed in the lumbar, thoracic, or cervical region, respectively, of the patient's spine. In one embodiment of strip electrodes, the strip electrodes are arranged to be used in more that one region of the patient's spine, each of the strip electrodes including a graded conductivity strip that causes voltage drops along the respective electrode strips so as to cause a decrease in voltage as the current moves along strip electrodes from the lumbar to the thoracic and/or from the thoracic to the cervical regions of the patient's spine.

BRIEF DESCRIPTION OF THE DRAWINGS

A system and method for electrically inducing osteogenesis in the spine in accordance with the invention is further described below with reference to the accompanying drawings, in which.

DETAILED DESCRIPTION OF THE INVENTION

Rat Model

Figure 1:
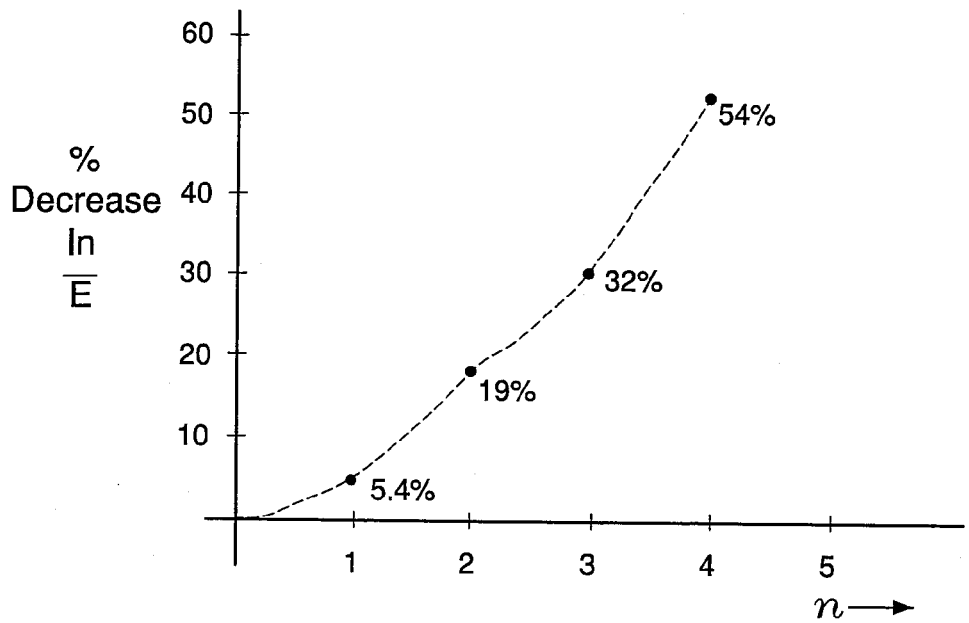
FIG. 1 illustrates the percentage decrease in mean electric field in trabecular bone of a neighboring vertebral body as a function of n, the number of vertebral bodies away from a single pair of transverse electrodes. For example, if the electrode (transverse pair) is over $L_1$, then n=1 describes $L_2$, n=2 describes $L_3$, etc.

A finite element study of Carter, Vresilovic, Pollack and Brighton was used to develop a rat model for the case of a single pair of electrodes in a transverse configuration. Using these results, the percent change in mean electric field amplitude in the trabecular bone of vertebral bodies was calculated as a function of distance from the transverse pair of electrodes. The result is shown in FIG. 1.

The computed value of any given electric field amplitude, as a function of the volume of trabecular bone tissue with that amplitude, is characterized by a distribution function with a half width of 43% of the mean value of the electric field amplitude experienced by the trabecular bone. This is shown in FIG. 2.

Figure 2:
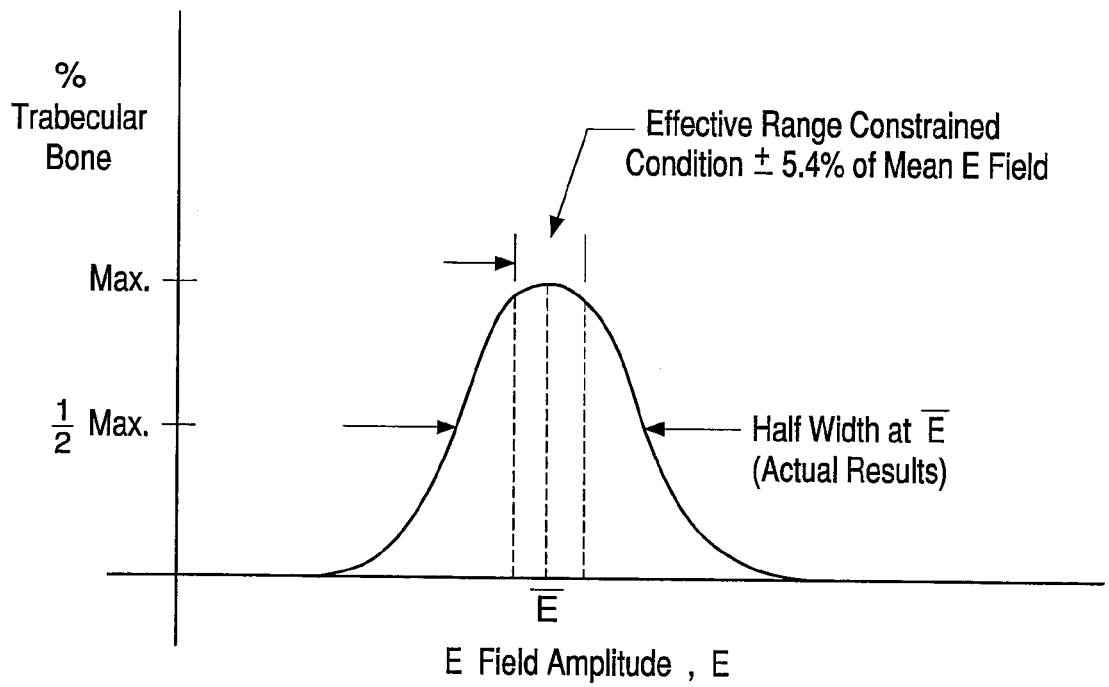
FIG. 2 illustrates that the computed value of any given electric field amplitude, as a function of the volume of trabecular bone tissue with that amplitude, is characterized by a distribution function with a half width of 43% of the mean value of the electric field amplitude experienced by the trabecular bone.
Figure 3:
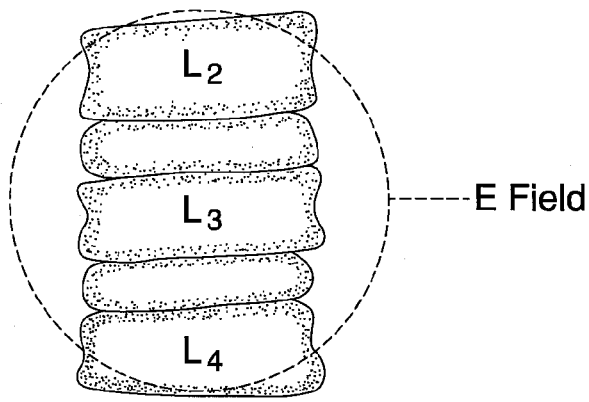
FIG. 3 illustrates the electric field E generated by a pair of electrodes in the transverse configuration centered about one vertebra ($L_3$, for instance) for use in fusing $L_2$–$L_3$ and $L_3$–$L_4$ with at least 94.6% of the mean E field.

If one imposes a constraint such that the mean electric field amplitude must remain within 5.4% of the value of the mean E field to be effective, then vertebral bodies could not be treated where the E field decreased below 5.4% of the mean E field (FIG. 2). In the rat model, that means that if the mean E field (E) value decreases by more than 5.4%, the technology will not be effective. As shown in FIG. 1, this means that if an electrode pair is adjacent to L, then the fields in trabecular bone of $L_4$ and $S_1$ will be 5.4% lower than in $L_5$, while the fields in trabecular bone of $L_3$ and $S_2$ will be reduced by 19%. Nineteen percent reduction in the mean electric field (E) is too great a reduction for clinical use. However, a reduction of 5.4% is acceptable as per the proposed constraint.

Accordingly, the result in the rat suggests that a pair of electrodes in the transverse configuration centered about one vertebra (L, for instance) could be used to fuse $L_2$–$L_3$ and $L_3$–$L_4$ with at least 94.6% of the mean E Field. However, if one wants to fuse multiple vertebral levels (3–10 or more, depending on the disease state), one pair of electrodes obviously will not work. The inventors considered two possible ways to increase the extent of an effective E field in the human vertebra: one is to use multiple electrode pairs with each pair powered by its own power supply but phased locked; the other solution is to use strip electrodes, one on each side of the spine, running the length of the vertebral segments to be fused.

Human Model

For the human model, the present inventors have developed a finite element modeling and analysis approach. In the human model, if a pair of electrodes is placed at the level of the $T_9$ vertebra, with the electrodes being on opposite sides of the spine and the center of each electrode being 5 cm from the midpoint of the underlying vertebral body, for 1.0 mA current input into the electrodes, the current density (mean value) is 1.10 $\mu A/cm^2 \pm 0.4$ $\mu A/cm^2$ (half width of mean current density value) for the inner cortical bone at $T_9$. At $T_7$ the value of the current density is reduced to 0.6 $\mu A/cm^2 \pm 0.2$ $\mu A/cm^2$ (half width of mean current density value) for the inner cortical bone. This result shows that for the human vertebrae that are two vertebrae away from the electrode the E field falls outside the half width of the treated vertebrae and, as in the rat model, the success rates may drop substantially if only a single pair of electrodes is used. For the above case, for outer cortical bone, the results are as follows: for the $T_9$ vertebra the mean current density for 1.0 mA current input into the electrodes is 1.5 $\mu A/cm^2 \pm 0.5$ $\mu A/cm^2$ half width, while at $T_9$ the mean current density is 1.0 $\mu A/cm^2 \pm 0.5$ $\mu A/cm^2$ half width. This reduction in the current density exceeds the 5.4% constraint and therefore will not work.

The effect of the location of the electrodes on the human body also has been considered by the inventors. For example, the inventors considered whether the same electric fields are equally effective in different parts of the body or, in this instance, the same in the lumbar versus the thoracic versus the cervical spine. The inventors discovered that the answer is no because current flow to the lumbar vertebra, for instance, will be reduced compared to that in the thoracic vertebrae because more current will flow to the abdominal region since its conductivity is higher. This can be seen below from actual finite elements studies.

Thoracic and Lumbar Vertebrae Current Densities:

In the $L_3$ lumbar vertebrae overlying the abdomen, for 1.0 mA current input into the electrodes, the current density in the abdomen is $4 \times 10^{-6}$ $\mu A/cm^2 \pm 1 \times 10^{-6}$ $\mu A/cm^2$, while for $T_7$ thoracic vertebrae overlying the lungs, the same current input into the electrodes would produce a current density in the thorax of $0.9 \times 10^{-6}$ $\mu A/cm^2 \pm 0.3 \times 10^{-6}$ $\mu A/cm^2$. However, the mean value of the current density in the vertebrae would be as follows:

$L_3$ mean current density=1.25 $\mu A/cm^2$ for 1 mA input $T_7$ mean current density=1.9 $\mu A/cm^2$ for 1 mA input This is a reduction in current density at $L_3$ of:

$$\frac{1.9 - 1.25}{1.9} \times 100 = 34\%$$

This reduction is due to the excess current that flows to the more conductive abdomen as seen above. The inventors conclude from this that the analysis must be separated between the abdomen ($L_1$–$L_5$) and the thorax $T_1$–$T_{12}$. Due to the presence of the lungs and ribs, the thorax has a higher resistivity. Therefore, for a given input current, more current flows near the back (spine) in the thorax than in the case of the abdomen. As a result, for a given input current to the lumbar vertebrae, the mean current that flows in the cortical bone of the vertebrae is about 34% lower than for the thorax.

The cervical (neck) spine will look more like the thorax but even more so because it has an even smaller volume through which current can flow in parallel with the current near the spine. Therefore, for a given current input from the electrodes at the cervical vertebra more current will flow in the vertebrae than in the thorax. For example, for a chest size of 36" and a neck size of 16" (circumference) the volume ratio per unit length is $(2.025)^2 = 4.1$. If the lungs occupy approximately half the volume of the thorax, this would reduce the ratio to 2.05. Taking cross sectional areas per unit length in the direction of current flow for transverse electrodes, this results in an increase in current to the bone portions of the spine in the neck by a factor of 1.5 over that in the thorax. Therefore, for the mean electric field to be the same in vertebrae in the three different regions (cervical, thoracic, lumbar), the input signal to the electrodes would have to vary as follows: for a 1.5 mA current input into an electrode pair with a transverse symmetric placement over the lumbar vertebrae, the electric input into electrodes with a transverse symmetric placement over thoracic vertebrae would be 1 mA current and overcervical vertebrae would be 0.67 mA. In this way the same current densities are produced in cortical and trabecular bone of vertebrae regardless of their anatomical location (cervical, thoracic, or lumbar).

If one wants to treat multiple vertebral levels and/or vertebral levels extending across more than one region of the spine (i.e., thoracolumbar), one has two choices: 1) use multiple pairs of electrodes (one pair for every 2 levels fused: thus, to fuse $L_1$ to $L_5$ two electrode pairs would be used with one pair centered over $L_2$ and one pair centered over $L_4$). The power unit would power multiple sets of electrodes and independently control the power output to reflect the number of vertebral levels fused and the location in the spine (i.e., lumbar, thoracic, or cervical) where the fusion is desired; or 2) use strip (continuous) electrodes, one strip electrode running vertically along the back on one side of the spine, and the other strip electrode running vertically along the back on the other side of the spine. The distance between the strips would be 10 cm (center to center).

Figure 4:
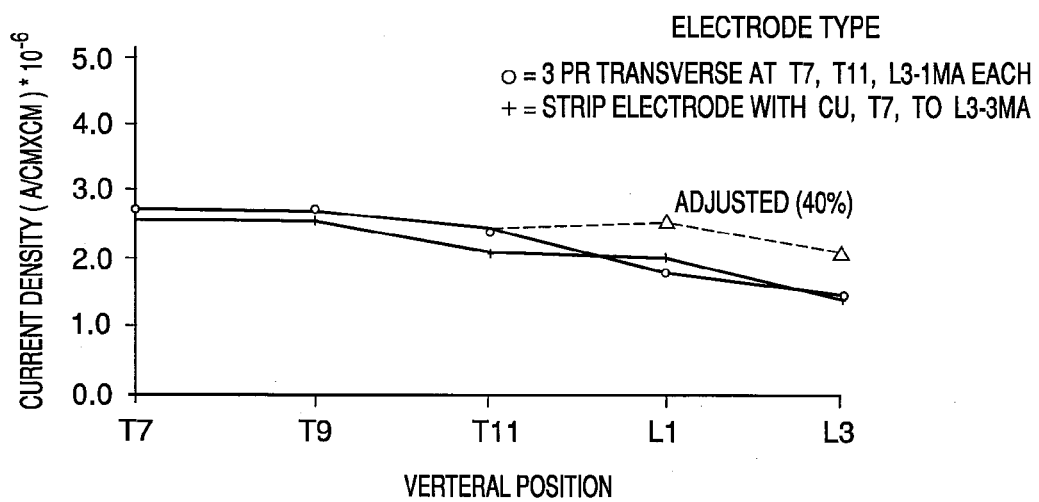
FIG. 4 illustrates the mean current density in the trabecular bone of the human model of the vertebrae as a function of vertebral position for current applied to different types of electrodes.

FIG. 4 demonstrates several things. The first is that discrete electrodes and strip electrodes with the same total current result in similar trabecular bone current densities in the vertebral bodies. The decrease in current density at $L_1$ and $L_3$ is the result of the above-described phenomenon associated with the lower over all electrical resistance of the abdomen relative to the thorax. As a result, the multiple pair device concept offers the opportunity to adjust the current level, say, in the pair over $L_3$ (see FIG. 4), increasing its value by approximately 40%, thereby achieving a nearly flat distribution (see FIG. 4) of current density values. Similar results obtain for cortical bone current densities. The remaining question is what current should be used for the various electrode types i.e. multiple pairs, strips of various length, regions that span multiple vertebral regions.

From the finite element study the present inventors know that placing a pair of electrodes over every other vertebra keeps within 5.4% of the mean field. The values for the mean current densities in the cortical bone and trabecular bone at $L_3$ with an electrode pair having a surface area of 6 cm² per electrode with a current of 1 mA are $1.14 \times 10^{-6}$ A/cm² and $1.54 \times 10^{-6}$ A/cm², respectively. Therefore, the clinical current density values using 7 mA to 10 mA are:

| Cortical Bone: | $7.98 \cdot 10^{-6}$ A/cm² to $11.4 \times 10^{-6}$ A/cm² |
|---|---|
| Trabecular Bone: | $10.8 \times 10^{-6}$ A/cm² to $15.4 \times 10^{-6}$ A/cm² |

The design of the power unit using multiple pairs should scale the current range for every second vertebra such that these values obtain. This will require a step-down of 33% in the current range to obtain the thorax value and a further 33% step down from the thorax value to obtain the value appropriate for the neck. The clinical values for electrode current (with an electrode pair centered over every second vertebra area) follow:

| Lumbar region | 7–10 mA |
|---|---|
| Thoracic region | 4.7–6.7 mA |
| Cervical region | 3.1–4.5 mA |

Of course, if the region to be treated is all the same, then only the currents for that region would be applied to the electrodes to achieve uniform current densities.

When using strip electrodes, one must consider whether all the vertebrae being treated are in the same region or whether the vertebrae being treated are from different regions. If all the vertebrae being treated are in the same region (i.e., lumbar region), then uniform (high) conductivity strip electrodes would have to increase in length as the number of vertebral levels to fuse increase. For example, in the lumbar region a two level fusion would require an input current of 7–10 mA to the electrode strips, a four level fusion would require an input current of 14–20 mA, a six level fusion of 21–30 mA, etc. However, this amount of current flow in these strip electrodes may be too dangerous to use clinically: any break or current leak in the electrodes might irritate or burn the patient's skin. To get around this unlikely but possible hazard, the electrode strips would be designed such that only 7–10 mA of current would be delivered to every two vertebra length of strip electrode. In other words, the electrode would be discontinuous, with every two level segment having its own current supply of 7–10 mA (for the lumbar region for example).

For strip electrodes to be used in more than one region, a graded conductivity strip is used so that the voltage drop along the electrode would result in a decrease in voltage as the current moved from the lumbar to the thorax or from the thorax to the neck region. In this configuration the input electrodes would enter the strip at the end of the electrode placed at the lumbar side (for lumbar-thorax fusion) or on the thorax side (for a thorax-neck fusion).

If pairs of individual electrodes are used rather than strip electrodes, the electronics must be designed so that the signal to all of the electrodes on a given side of the body are phase locked to assure that one side, say the right side, is all positive while the left side is all negative and vice versa. In addition, the amplitude of the current should be adjusted as per the above analysis depending upon the location on the body of each pair of electrodes used.

Device Design:

Multiple Electrode Pairs

Figure 5:
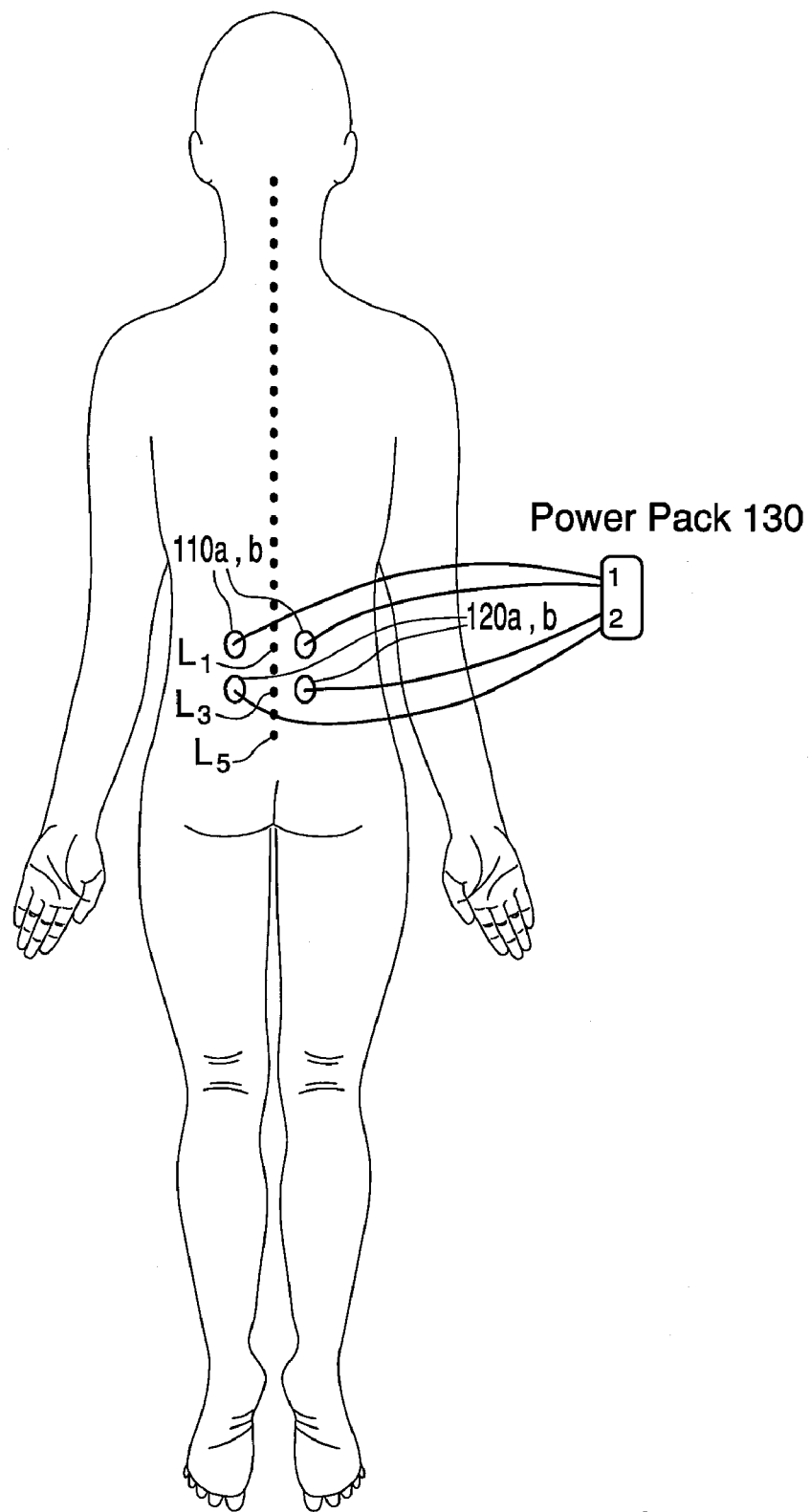
FIG. 5 illustrates electrode placement for a 4-level fusion using two electrode pairs in accordance with a first embodiment including electrode pairs in accordance with the invention.

FIG. 5 illustrates electrode placement for a 4-level fusion using two electrode pairs 110a, 110b and 120a, 120b in accordance with a first embodiment of the invention. Each electrode 110a, 110b, 120a, 120b has a surface area of 6 cm² and is self-adherent. The power device 130 is run on one 9-volt battery and has resistors/transistors or current chip so designed that each pair of electrodes plugged into the device delivers the pre-selected amount of current as set by a switch on the device (C or cervical, T for thoracic, and L for lumbar). For example, when switched to C, the electrode pair delivers 3.4–4.5 mA of current, when switched to T it delivers 4.7–6.7 mA, and when switched to L it delivers 7–10 mA of current. The device may include multiple ports, each a plug-in for an electrode pair, and each controlled by a switch to indicate region of treatment. In FIG. 5, the first pair of electrodes 110a, 110b are shown as centered over $L_1$ for fusing $T_{12}$–$L_1$ and $L_1$–$L_2$. For this purpose, 7–10 mA of current is provided at port 1. Similarly, the second pair of electrodes 120a, 120b are shown as centered over $L_3$ for fusing $L_2$-$L_3$ and $L_3$-$L_4$. For this purpose, 7–10 mA of current is provided at port 2. A switch (not shown) within the power device 130 may be used to select the appropriate current to be applied to each port based on the treatment area to which the inserted electrode pair is applied.

Strip electrodes

Figure 6:
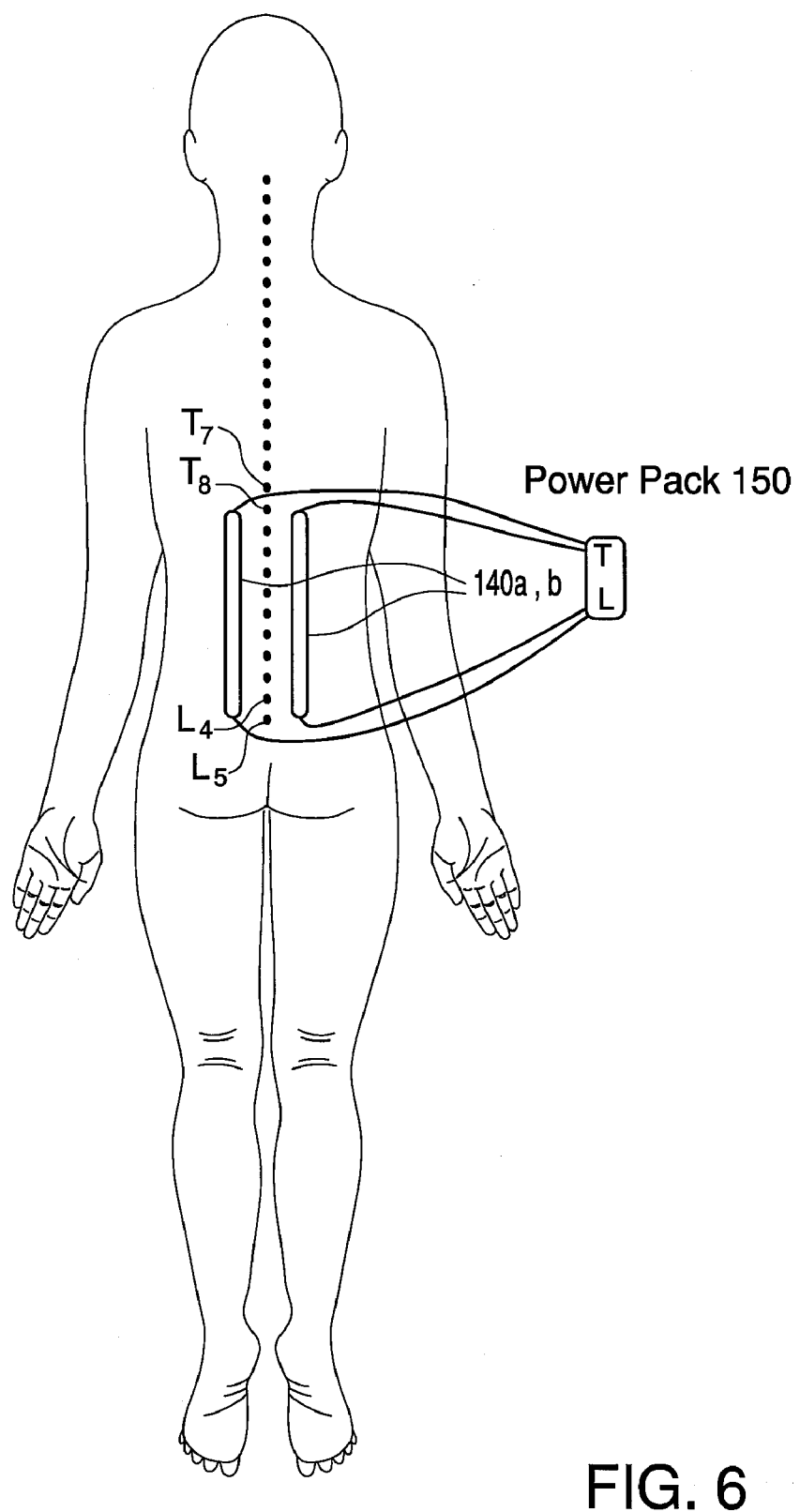
FIG. 6 illustrates strip electrode placement for multiple spine level fusion in accordance with a second embodiment including strip electrodes in accordance with the invention.

FIG. 6 illustrates strip electrode placement for multiple spine level fusion using strip electrodes 140a, 140b in accordance with a second embodiment of the invention. Each strip electrode 140a, 140b is 2.5 cm wide. The length varies according to the number of vertebral levels to be fused (3 to 15), allowing 3 cm per vertebral level. Thus, the electrode strips 140a, 140b may vary from 9 cm to 45 cm long. Strip electrodes for each region (lumbar, thoracic, cervical spine) may be separate and plug into the appropriately marked port on the power device 150. The power device 150 is designed such that each region would receive the amount of current for that region (e.g., 7–10 mA for L, 4.7–6.7 mA for T, and 3.4–4.5 mA for C). The power device 150 runs on a 9-volt battery and has resistors, transistors, and/or circuit chips such that the region treated may be selected by switch as well as the number of vertebral levels, keeping in mind that every 6 cm of strip length would receive only those current levels designated for each region above. In other words, every 6 cm of strip length would be a complete circuit and would deliver one of the current levels cited above, depending on the region. As illustrated, power device 150 may produce a current of 4.7–6.7 mA at port T for generation of an electric field for application to the thoracic vertebrae ($T_7$–$T_{12}$) and a current of 7–10 mA at port L for generation of an electric field for application to the lumbar vertebrae ($L_1$–$L_5$). A port C may also be provided on power device 150 for generating current to apply to cervical vertebrae. A switch (not shown) within the power device 150 may be used to select the appropriate current to be applied to each port based on the area of the spine treated by that port.

The description provided herein deals specifically with the current values to the multiple electrodes or strip electrodes. As in the aforementioned patent, the voltage and signal characteristics are the 20 kHz to 100 kHz, 60 kHz, 5 to 10 volts peak to peak sine wave (symmetric) and non-symmetric variations of these quantities. Those skilled in the art will appreciate that other variations in these values may also lead to useful clinical results.

Although exemplary implementations of the invention have been described in detail above, those skilled in the art will readily appreciate that many additional modifications are possible in the exemplary embodiments without materially departing from the novel teachings and advantages of the invention. Any such modifications are intended to be included within the scope of this invention as defined by the following exemplary claims.

We claim:

1. A method of electrically inducing osteogenesis in the spine of a patient, comprising the steps of:
    placing a pair of electrodes on respective sides of the patient's spine; and
    applying at least one of a first electrical signal to the pair of electrodes when the pair of electrodes is placed in a treatment area of the lumbar region of the patient's spine, a second electrical signal to the pair of electrodes when the pair of electrodes is placed in a treatment area of the thoracic region of the patient's spine, and a third electrical signal to the pair of electrodes when the pair of electrodes is placed in a treatment area of the cervical region of the patient's spine, wherein the first, second, and third electrical signals are each effective to induce osteogenesis in the respective treatment areas of the patient's spine, and wherein the first, second, and third electrical signals respectively generate different electrode currents in the respective treatment areas.

2. The method of claim 1, wherein a pair of electrodes is placed on respective sides of the patient's spine in each of the lumbar, thoracic and cervical regions of the patient's spine and wherein the first, second and third electrical signals are simultaneously applied to the respective electrodes in the respective treatment areas to create current densities that are approximately equal in the respective treatment areas.

3. The method of claim 1, wherein the electrodes are placed on the patient's skin.

4. The method of claim 1, wherein the electrodes comprise respective pairs of electrodes placed in each of said treatment areas in said placing step.

5. The method of claim 1, wherein the electrodes comprise respective strip electrodes each placed in said placing step so as to run vertically along the back on respective sides of the patient's spine.

6. The method of claim 1, wherein a current stimulated by the first electrical signal is greater than the current stimulated by the second electrical signal, and the current stimulated by the second electrical signal is greater than the current stimulated by the third electrical signal.

7. The method of claim 6, wherein the current stimulated by the second electrical signal is approximately ⅔ the current stimulated by the first electrical signal, and the current stimulated by the third electrical signal is approximately ⅔ the current stimulated by the second electrical signal.

8. The method of claim 7, wherein the electrode current stimulated by the first electrical signal is in the current range of 7–10 mA, the electrode current stimulated by the second electrical signal is in the current range of 4.7–6.7 mA, and the electrode current stimulated by the third electrical signal is in the current range of 3.1–4.5 mA.

9. A device for electrically inducing osteogenesis in the spine of a patient, comprising:
    a pair of electrodes adapted for application on respective sides of the patient's spine in respective treatment regions of the patient's spine; and
    a power source that is adapted to selectively apply a first electrical signal to the electrode pair when applied in a treatment area of the lumbar region of the patient's spine, a second electrical signal to the electrode pair when applied in a treatment area of the thoracic region of the patient's spine, and a third electrical signal to the electrode pair when placed in a treatment area of the cervical region of the patient's spine, wherein the first, second, and third electrical signals are each effective to induce osteogenesis in the respective treatment areas of the patient's spine and wherein the first, second, and third electrical signals respectively generate different electrode currents in the respective treatment areas.

10. The device of claim 9, wherein a pair of electrodes is placed on respective sides of the patient's spine in each of the lumbar, thoracic and cervical regions of the patient's spine and wherein the first, second and third electrical signals are simultaneously applied to the respective electrode pairs in the respective treatment areas by the power source to create current densities that are approximately equal in the respective treatment areas and such that all electrodes on one side of the patient's spine are all positive while all electrodes on another side of the patient's spine are all negative.

11. The device of claim 9, wherein the electrode pair is adapted to be attached to the patient's skin and to apply the electrode currents to the patient's spine through capacitive coupling.

12. The device of claim 9 wherein a current stimulated by the first electrical signal is greater than the current stimulated by the second electrical signal, and the current stimulated by the second electrical signal is greater than the current stimulated by the third electrical signal.

13. The device of claim 12, wherein the current stimulated by the second electrical signal is approximately ⅔ the current stimulated by the first electrical signal, and the current stimulated by the third electrical signal is approximately ⅔ the current stimulated by the second electrical signal.

14. The device of claim 13, wherein the electrode current stimulated by the first electrical signal is in the current range of 7–10 mA, the electrode current stimulated by the second electrical signal is in the current range of 4.7–6.7 mA, and the electrode current stimulated by the third electrical signal is in the current range of 3.1–4.5 mA.

15. The device of claim 9, wherein the power source generates said first, second and third electrical signals and said device further comprises at least one switch that selectively applies said first, second or third electrical signals to the electrode pair in accordance with the treatment area of the spine in which the electrode pair is placed.

16. The device of claim 15, further comprising respective plug-in ports for respective electrode pairs, each electrode pair controlled by a switch that is adjusted in accordance with the treatment area to which the electrode pair is to be applied.

17. A device for electrically inducing osteogenesis in the spine of a patient, comprising:
respective strip electrodes for application on either side of the patient's spine so as to run vertically along the patient's back on respective sides of the patient's spine; and
a power source that selectively applies a first electrical signal to the strip electrodes when the strip electrodes are placed in a treatment area of the lumbar region of the patient's spine, a second electrical signal to the strip electrodes when the strip electrodes are placed in a treatment area of the thoracic region of the patient's spine, and a third electrical signal to the strip electrodes when the strip electrodes are placed in a treatment area of the cervical region of the patient's spine, wherein the first, second, and third electrical signals are each effective to induce osteogenesis in the respective treatment areas of the patient's spine, and wherein the first, second, and third electrical signals respectively generate different electrode currents in the respective treatment areas.

18. The device of claim 17, wherein the strip electrodes are arranged such that a selected amount of current for each respective treatment area is delivered to the strip electrodes such that every two-vertebra length of the strip electrodes in the respective treatment areas receives the selected amount of current for that respective treatment area.

19. The device of claim 18, wherein the strip electrodes are discontinuous and each two vertebra length of the strip electrodes receives one of the first, second and third electrical signals from the power source based on whether the two vertebra length is placed in the lumbar, thoracic, or cervical region, respectively, of the patient's spine.

20. The device of claim 17, wherein the strip electrodes are arranged to be used in more than one region of the patient's spine, each of said strip electrodes including a graded conductivity strip that causes voltage drops along the respective electrode strips so as to cause a decrease in voltage as the current moves along strip electrodes from the lumbar to the thoracic and/or from the thoracic to the cervical regions of the patient's spine.

21. The device of claim 17, wherein the strip electrodes are adapted to be attached to the patient's skin and to apply the electrode currents to the patient's spine through capacitive coupling.

22. The device of claim 17, wherein a current stimulated by the first electrical signal is greater than the current stimulated by the second electrical signal, and the current stimulated by the second electrical signal is greater than the current stimulated by the third electrical signal.

23. The device of claim 22, wherein the current stimulated by the second electrical signal is approximately ⅔ the current stimulated by the first electrical signal, and the current stimulated by the third electrical signal is approximately ⅔ the current stimulated by the second electrical signal.

24. The device of claim 23, wherein the electrode current stimulated by the first electrical signal is in the current range of 7–10 mA, the electrode current stimulated by the second electrical signal is in the current range of 4.7–6.7 mA, and the electrode current stimulated by the third electrical signal is in the current range of 3.1–4.5 mA.

25. The device of claim 17, wherein a separate pair of strip electrodes is provided for the lumbar, thoracic and cervical regions of the patient's spine, the power source comprising respective ports and at least one switch that selectively applies said first, second or third electrical signals to said respective ports in accordance with the treatment area of the spine in which the respective electrode pairs are placed.

* * * * *